United States Patent
Tsuyuki et al.

[11] Patent Number: 5,876,327
[45] Date of Patent: Mar. 2, 1999

[54] IMAGING APPARATUS FOR ENDOSCOPES

[75] Inventors: Hiroshi Tsuyuki; Masami Shimizu, both of Hachioji, Japan

[73] Assignee: Olympus Optical Co., Ltd., Tokyo, Japan

[21] Appl. No.: 922,473

[22] Filed: Sep. 3, 1997

[30] Foreign Application Priority Data

Sep. 3, 1996 [JP] Japan .................................. 8-233166
Jul. 4, 1997 [JP] Japan .................................. 9-179797

[51] Int. Cl.$^6$ .................................................. A61B 1/06
[52] U.S. Cl. .......................... 600/112; 600/167; 600/180; 600/181
[58] Field of Search ............................. 600/167, 163, 600/180, 181, 112

[56] References Cited

U.S. PATENT DOCUMENTS

| | | | |
|---|---|---|---|
| 4,685,450 | 8/1987 | Collins | 600/112 |
| 4,697,894 | 10/1987 | Takamura | 600/112 |
| 4,777,524 | 10/1988 | Nakajima | 600/167 |
| 4,868,645 | 9/1989 | Kobayashi | 600/181 |
| 4,916,534 | 4/1990 | Takahashi | 600/181 |
| 4,967,269 | 10/1990 | Sasagawa | 600/180 |
| 4,987,884 | 1/1991 | Nishioka | 600/181 |
| 5,056,902 | 10/1991 | Chinnock | 600/112 |
| 5,101,807 | 4/1992 | Kawashima | 600/112 |
| 5,150,702 | 9/1992 | Miyanaga | 600/181 |
| 5,159,380 | 10/1992 | Furuya | 600/180 |
| 5,179,934 | 1/1993 | Nagayoshi | 600/167 |
| 5,222,477 | 6/1993 | Lia | 600/181 |
| 5,609,563 | 3/1997 | Suzuki | 600/167 |

FOREIGN PATENT DOCUMENTS 7-234365  9/1995  Japan .

Primary Examiner—Gene Mancene
Assistant Examiner—Ira Hatton
Attorney, Agent, or Firm—Pillsbury Madison & Sutro LLP

[57] ABSTRACT

An imaging apparatus for endoscopes includes an endoscope relaying an object image through an observing optical system, and an imaging section removably mounted to the rearmost end of the endoscope, including a stop unit provided with a variable stop capable of changing an aperture size thereof, an imaging lens system, a focus lens system, and an image sensor. The relative positions of the variable stop, the imaging lens system, and the image sensor are constant, and the focus lens system can be moved along the optical axis of the imaging section. In this way, the imaging apparatus for endoscopes can be provided which is simple in structure, small in size, and low in cost.

15 Claims, 11 Drawing Sheets

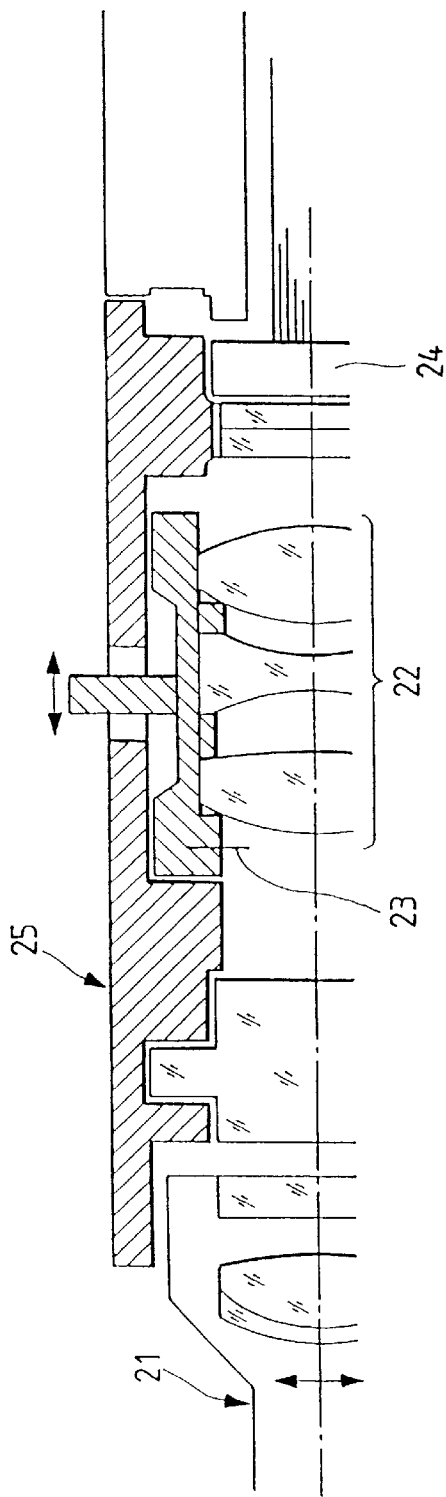
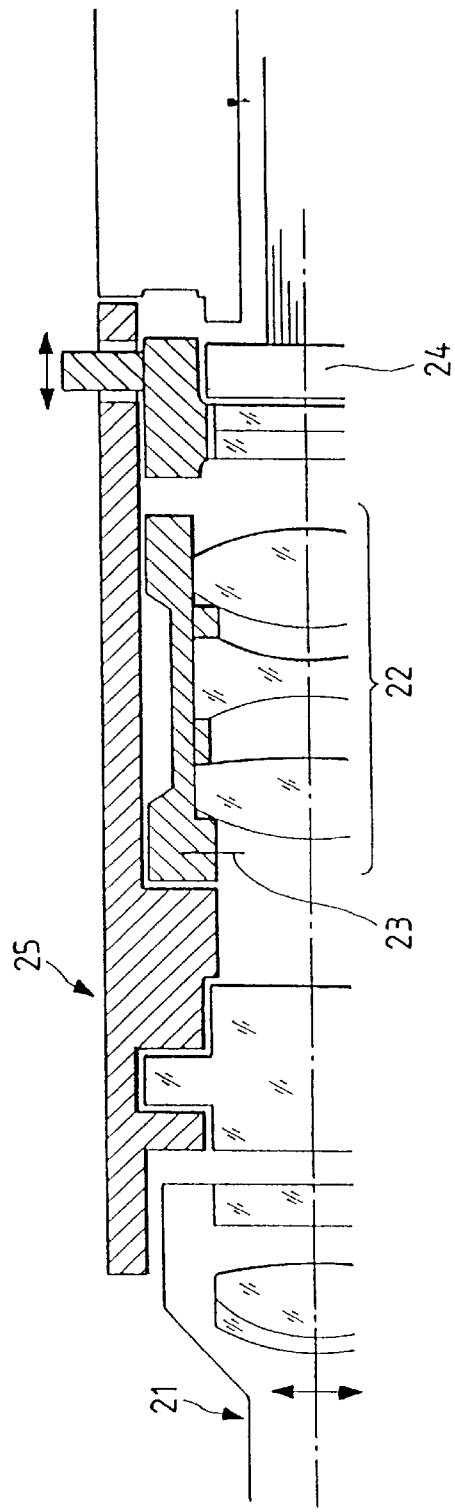

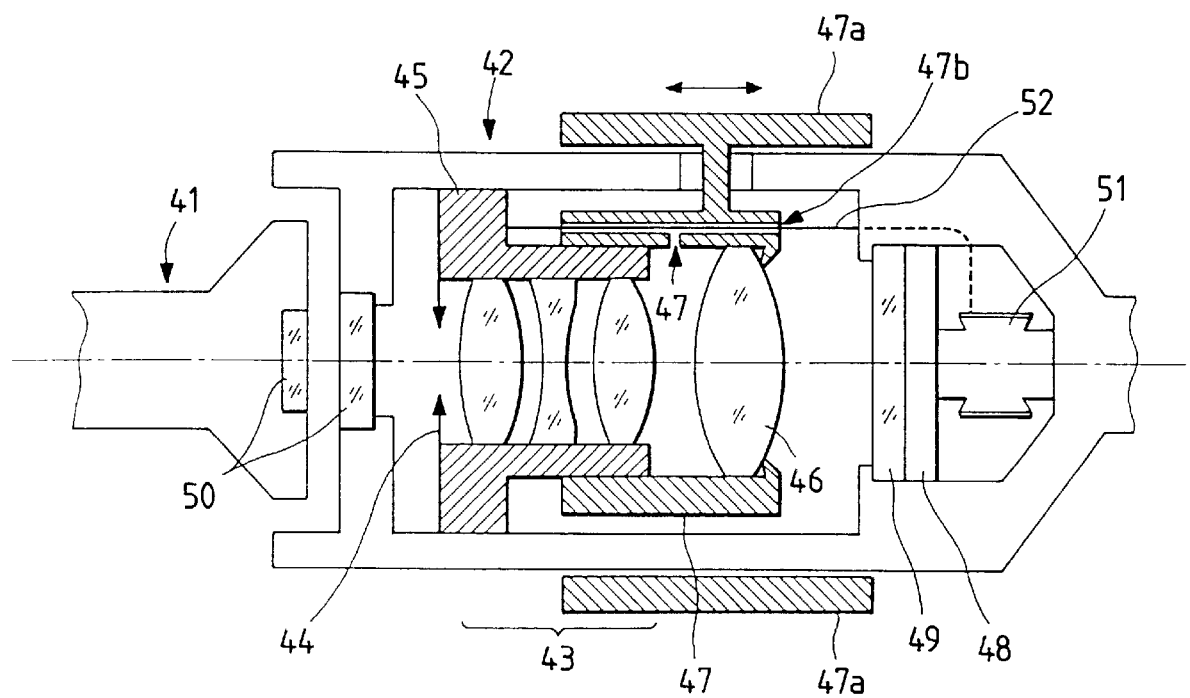

IMAGING APPARATUS FOR ENDOSCOPES

BACKGROUND OF THE INVENTION

1. Field of the Invention

This invention relates to an imaging apparatus for endoscopes which includes an endoscope and an imaging section having the function of a TV camera and allows an image derived from the endoscope to be observed through a TV monitor.

2. Description of Related Art

In general, where an image inside the human body which is derived from an endoscope is displayed on a TV monitor for observation, an imaging apparatus is used which has a TV camera removably mounted to the rear of an eyepiece section of the endoscope.

Imaging apparatuses for endoscopes of this type are various in optical arrangement. As an example, an imaging apparatus for endoscopes disclosed in Japanese Patent Preliminary Publication No. Hei 7-234365 may be cited. FIG. 1 shows the arrangement of this imaging apparatus. The imaging apparatus includes an adapter 13 removably mounted to the eyepiece section of an endoscope 11, having a focus lens 12 for changing the degree of convergence or divergence of a beam of light emerging from the eyepiece section, and a TV camera 17 of watertight structure which is removably mounted to the adapter 13 and has a variable stop 14, an imaging lens system 15, and an image sensor 16. In this way, the imaging apparatus is designed so that when the TV camera 17 is attached through the adapter 13 to the eyepiece section of the endoscope 11, a distance between the adapter 13 and the TV camera 17 is changed and thereby a focusing operation is performed.

FIGS. 2A and 2B show arrangements of conventional imaging apparatuses for endoscopes. Each of these imaging apparatuses is equipped with an endoscope 21 and a TV camera head 25 which has an imaging lens system 22 for re-forming an object image relayed, as a final image, by the endoscope 21, stop means 23 variable in aperture size, and an image sensor 24. The relative positions of at least one of lenses constituting the imaging lens system 22 and the stop means 23 are kept constant with respect to the optical axis. In FIG. 2A, the imaging lens system 22 and the variable stop 23 are moved along the optical axis, while in FIG. 2B, the image sensor 24 is moved. In either case, an axial distance between the one lens of the imaging lens system 22 and the image sensor 24 is changed and thereby the focusing operation is performed.

FIG. 3 depicts the arrangement of a TV photographic adapter constituting a conventional imaging apparatus for endoscopes. A TV photographic adapter 31 includes an imaging lens system 32, a variable stop 33, a power supply 34 for actuating the variable stop 33, a light-receiving element 35 for controlling the variable stop 33, and a variable stop control device 36. This adapter is hermetically sealed through sapphire glass covers 37. Although the TV photographic adapter 31, when used, is connected, together with a TV camera, not shown, to the endoscope, the focusing operation is performed by means of the same mechanism as in FIG. 1.

In the imaging apparatus for endoscopes, it is desirable that the stop is placed close to the exit pupil of the endoscope. This is because if the stop is disposed farther away from the exit pupil, a light beam passing through the stop will give rise to vignetting, and the quality of a resultant image will be deteriorated.

With the imaging apparatus shown in FIG. 1, when the focusing operation is performed, the position of the stop in the imaging apparatus for endoscopes is varied, and hence a chief ray passing through the lens system is shifted from the position where the optimum condition is obtained, that is, aberrations are most favorably corrected. Consequently, an image may suffer deterioration in quality, which is not favorable. Furthermore, the imaging apparatus provides the adapter 13 with a focusing function and thus requires a large number of parts. This fact is disadvantageous to costs.

The imaging apparatus shown in FIG. 2A, which is constructed so that the stop means 23 is moved, together with the imaging lens system 22, along the optical axis, is unfavorable for use because the relative positions of the stop means 23 and the exit pupil of the endoscope 21 are shifted to thereby cause variations of aberrations as in the imaging apparatus of FIG. 1. In order to drive the stop means 23 directly, the imaging apparatus requires a multiple frame structure (at least two frames, one for fixing the stop means 23 and the imaging lens system 22 and the other for the focusing operation), with a resulting increase in manufacturing cost. Moreover, since the stop means 23 is moved, together with a unit holding the stop means 23, along the optical axis, there is the fear that a signal line, not shown, is broken which is connected to the stop means 23 to transmit a signal for controlling the aperture size thereof.

On the other hand, the imaging apparatus shown in FIG. 2B, which is such that the image sensor 24 is moved along the optical axis in the focusing operation, requires a length of fit or a unit including the imaging lens system 22 to be increased to some extent so that optical misalignment of the entire lens system is obviated. This brings about an unfavorable shape for the imaging apparatus for endoscopes requiring lightweight and compact design. Additionally, by moving the image sensor 34, an unnecessary load is applied to a flexible printed circuit board provided at the rear end thereof, and hence there is the possibility that the flexible printed circuit board will be damaged.

The TV photographic adapter 31 of the imaging apparatus for endoscopes shown in FIG. 3 is equipped with the power supply 34 for actuating the variable stop 33 and the control device 36, which form the key elements that prevent lightweight and compact design required for the imaging apparatus for endoscopes. Thus, this arrangement is unfavorable. The focusing means of this apparatus has the same problem as that of the apparatus shown in FIG. 1.

SUMMARY OF THE INVENTION

It is, therefore, an object of the present invention to provide an imaging apparatus for endoscopes which gives rise to a large depth of field through a variable stop, and which is small in size and simple in structure, but is capable of performing an optimum focusing operation and brings about a good image.

In order to achieve this object, according to one aspect of the present invention, the imaging apparatus for endoscopes includes an endoscope for relaying an object image through an observing optical system and an imaging section which is removably mounted to the rear end, situated on the image side, of the endoscope and is comprised of a stop unit having a variable stop whose aperture size is variable, an imaging lens system, a focus lens system, and an image sensor. The relative positions of the variable stop, the imaging lens system, and image sensor are constant, but the focus lens system can be moved along the optical axis.

According to another aspect of the present invention, the imaging lens system of the imaging apparatus for endoscopes is held in the stop unit.

According to still another aspect of the present invention, the focus lens system of the imaging apparatus for endoscopes is held in a focus lens frame, into which the stop unit is fitted.

According to a further aspect of the present invention, the focus lens frame of the imaging apparatus for endoscopes has a through-hole for a signal line which transmits a signal for controlling the aperture size of the variable stop.

This and other objects as well as the features and advantages of the present invention will become apparent from the following detailed description of the preferred embodiments when taken in conjunction with the accompanying drawings.

BRIEF DESCRIPTION OF THE DRAWINGS

FIG. 2A is a sectional view, developed along the optical axis, showing another example of the arrangement of the conventional imaging apparatus for endoscope;

FIG. 2B is a sectional view, developed along the optical axis, showing still another example of the arrangement of the conventional imaging apparatus for endoscopes;

FIG. 4 is a sectional view, developed along the optical axis, showing the fundamental arrangement of the imaging apparatus for endoscopes according to the present invention;

FIG. 5 is a view for explaining a pixel pitch in a horizontal scanning direction of a CCD used in the imaging apparatus for endoscopes of the present invention;

DETAILED DESCRIPTION OF THE PREFERRED EMBODIMENTS

Figure 1:
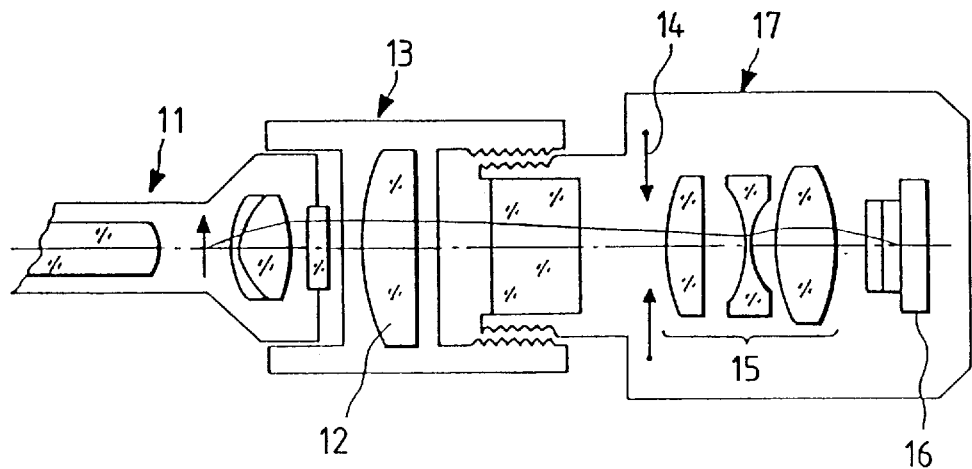
FIG. 1 is a sectional view, developed along the optical axis, showing an example of the arrangement of a conventional imaging apparatus for endoscopes.
Figure 3:
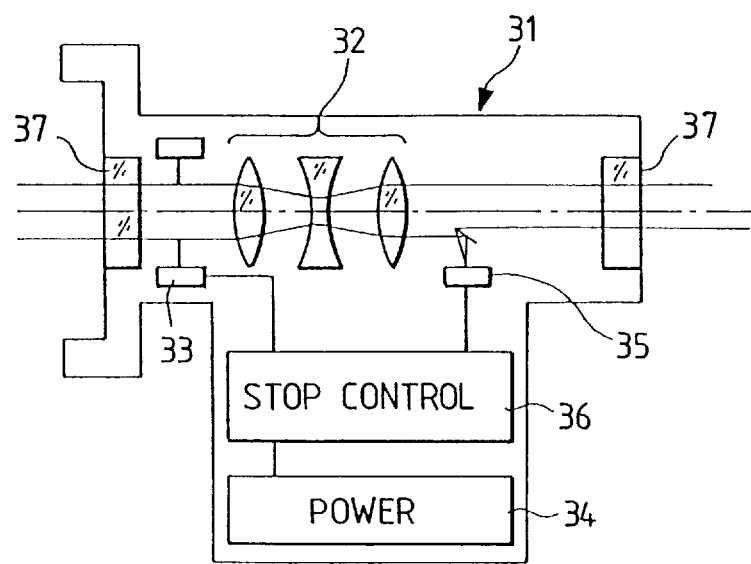
FIG. 3 is a view showing the arrangement of a TV photographic adapter constituting the conventional imaging apparatus for endoscopes.

Before undertaking the description of the embodiments, it will be expedient to explain the function of the imaging apparatus for endoscopes of the present invention.

The imaging apparatus for endoscopes of the present invention, as shown in FIG. 4, includes an endoscope 41 and an imaging section 42 removably mounted to the eyepiece section of the endoscope 41. The imaging section 42 is constructed with an imaging lens system 43; an elongated, cylindrical stop unit 45 which holds the imaging lens system 43 and has a variable stop 44; a focus lens frame 47 which has a focus lens system 46 and into which the stop unit 45 is fitted; a charge coupled device image sensor (CCD) 48; and a filter unit 49 placed immediately before the CCD 48. The focus lens frame 47 is provided with a focus ring 47a.

The variable stop 44 includes a stop blade portion for changing its aperture size and a driving device, not shown, for driving the stop blade portion, and is connected through a signal line 52 to a flexible printed circuit board 51 situated at the rear end of the CCD 48. The signal line 52 is passed through a through-hole 47b bored in the focus lens frame 47. The focus lens frame 47 has an air hole 47c communicating with the through-hole 47c to adjust air pressure in the focus lens frame 47 when the focusing operation is performed.

The surface of the imaging section 42 connected with the endoscope 41, as well as that of the eyepiece section of the endoscope 41, is provided with a glass cover 50 made of crystal glass with the at resistance, such as sapphire ($Al_2O_3$), quartz, rock crystal, etc. In this way, each of the endoscope 41 and the imaging section 42 is hermetically sealed and thus can be treated by autoclaving.

In the imaging apparatus for endoscopes of the present invention, an object image transmitted from the eyepiece section of the endoscope 41 is restricted in brightness by the variable stop 44, and is formed, through the filter unit 49, on the CCD 48 by the imaging lens system 43 and the focus lens system 46. In the imaging section 42, since the imaging lens system 43 and the variable stop 44 are supported by the stop unit 45 and the CCD 48 is fixed, the relative positions of the imaging lens system 43, the variable stop 44, and the CCD 48 are constant. When the imaging section 42 is mounted to the eyepiece section of the endoscope 41, the stop unit 45 is positioned so that the variable stop 44 is located close to the exit pupil of the endoscope 41. The focusing operation of the imaging apparatus is performed in such a way that the focus ring 47a attached to the focus lens frame 47 is operated in directions of arrows of the figure from the outside or the imaging section 42 to move the focus lens system 46, together with the focus lens frame 47, along the optical axis.

The aperture diameter of the variable stop 44 is adjusted in accordance with illuminance of the surface of the object image formed on the CCD 48. Specifically, in the CCD 48, the illuminance of the object image formed thereon is converted into an electric signal, which is transmitted, through the flexible printed circuit board 51 situated at the rear end of the CCD 48 and the signal line 52, to a driving device constituting the variable stop 44. In this way, the aperture diameter of the variable stop 44 is set by the driving device.

Since the imaging apparatus for endoscopes of the present invention, unlike the conventional one, is designed so that the stop unit 45 and the CCD 48 are fixed in the imaging section 42, it is avoidable that the flexible printed circuit board 51 and the signal line 52 are subjected to unnecessary loads when the focusing operation is performed. Furthermore, the signal line 52 is passed through the through-hole 47b bored in the focus lens frame 47, and thus friction between the signal line 52 and the focus lens frame 47 is kept to a minimum.

The stop unit 45 shaped into an elongated, cylindrical form is also used as a frame for the imaging lens system 43, thus doing away with the need for a separate lens frame. This is effective for compactness of the apparatus. Moreover, because the stop unit 45 is fitted into the focus lens frame 47, misalignment of the optical system can be obviated. Where a length sufficient to fit the stop unit 45 into the focus lens frame 47 cannot be obtained, for example, the CCD 48 may be fixed by the use of a frame member so that tile frame member is fitted into the focus lens frame 47, unless the misalignment of the optical system is caused.

In general, as a ray of light separates from a stop, the height of the ray at a lens system increases progressively, as a matter of course. Thus, even with the apparatus of the present invention, there is the fear that rays are eclipsed by the edge of the focus lens system 46, or the focus lens frame 47, located at a position relatively distant from the variable stop 44. The eclipse of the rays are unfavorable because it brings about the vignetting of the object image, or detrimental rays such as flare. In view of this respect, the apparatus of the present invention is constructed so that the outside diameter of the focus lens system 46 is equal to or larger than that of the imaging lens system 43 to such an extent that the apparatus is not very bulky. If it is structurally difficult to obtain such an outside diameter of the focus lens system 46, for example, a flare stop may be placed close to the focus lens system 46 or in the imaging lens system 43.

The primary function of the focus lens system 46 is not to correct for aberration but to make a focus adjustment and acquire telecentric properties of light incident on the CCD 48. Thus, the focus lens system 46 need not necessarily be constructed with a plurality of lenses. In view of cost reduction, work efficiency of assembly, and control of variation in product, it is desirable that this lens system be a single lens.

Further, where account is taken of the amount of lens movement in the focusing operation, if a plurality of lenses are arranged in the focus lens system 46, the entire length of the imaging section 42 must be increased. It is thus desirable that the focus lens system 46 be a single lens. However, unless the imaging section 42 is restricted in its size, the focus lens system 46 need not necessarily be a single lens and may be constructed with a plurality of lenses, for example, in order to correct for aberration with a high degree of accuracy.

Additionally, it is favorable that the focus lens system 46 has a positive power. It is for this reason that the telecentric properties of incident light on the CCD 48 are acquired. Unless the telecentric properties are acquired, that is, unless an angle of incidence of a chief ray on the CCD 48 is practically perpendicular to its light-receiving surface, a problem, such as luminance shading or color shading, will arise.

If the focus lens system 46 has a negative power, it becomes difficult to obtain the telecentric properties. This is because the focal length of the entire lens system must be constant and thus the positive power of the imaging lens system 43 needs to be increased, but in this case, there is the fear that a ray height at the rearmost lens of the imaging lens system 43 is considerably increased, causing vignetting of rays or oversizing of the lens. If, in this state, an attempt is made to forcedly lower the ray height at the rearmost lens of the imaging lens system 43, it may be expected that the focal length of the entire lens system ceases to be kept constant or deterioration of aberration without a tolerance is caused. Moreover, to avoid this problem, if the imaging lens system 43 is provided with many positive lenses, thereby dispersing the positive power of tile imaging lens system 43, namely weakening the positive power of each lens, the entire length of the imaging lens system 43 will be unfavorably increased.

For the above reasons, it is desirable that the focus lens system 46 be constructed with a single positive lens.

In the imaging apparatus for endoscopes of the present invention, when the focal length of the imaging lens system 43 is denoted by $f_o$ and the focal length of the focus lens system 46 is denoted by $f_a$, it is desirable to satisfy the condition:

$$0.05 < |f_a/f_o| < 0.35 \qquad (1)$$

If the value of $|f_a/f_o|$ is below the lower limit of Eq. (1), the focal length of the imaging lens system 43 will be excessively increased, and thus there is the fear of causing the deterioration of aberration in the imaging lens system 43 or the vignetting of rays in the focus lens system 46. In this case, to maintain the telecentric properties of incident light on the CCD 48, the focal length of the focus lens system 46 must be reduced. Moreover, the focus lens system 46 in this case requires such a shape that the working of the lens is very difficult.

On the other hand, if the value of $|f_a/f_o|$ passes the upper limit of Eq. (1), the focal length of the focus lens system 46 will be excessively increased, and it becomes difficult to maintain the telecentric properties. Alternatively, the focal length of the imaging lens system 43 becomes very short, and thus each of lenses constituting the imaging lens system 43 is liable to take such a shape that the working of the lens is very difficult. This is unfavorable. Also, in order to correct for axial chromatic aberration and chromatic aberration of magnification, it is effective to use a cemented lens in the imaging lens system 43.

In general, when variable stops are manufactured, it is imperative that manufacturing errors are produced, to some extent, in all products even where they are manufactured on the basis of the same specification. That is, the maximum and minimum aperture diameters of the variable stops vary with products. Here, a description will be given of conditions to be satisfied when the aperture size of the variable stop 44 is changed to increase the depth of field in the imaging apparatus of the present invention.

When φ denotes the minimum limit value of the aperture diameter of the variable stop 44, f denotes the total focal length of an optical system placed behind the variable stop 44, and Px denotes the pitch of pixels in a horizontal scanning direction of the CCD 48, it is desirable that the imaging apparatus for endoscopes of the present invention satisfies the condition:

$$\phi \geq 2.15 \times 10^{-4} f/Px \qquad (2)$$

In the imaging apparatus for endoscopes of the present invention, if the aperture diameter of the variable stop 44 is made extremely small, a reduction in resolving power will be caused by the diffraction limit of light, and the effect of improvement of the depth of field cannot be brought about even though the variable stop 44 is stopped down. Thus, in order to obviate this problem, it is necessary to define Eq. (2) which gives the optimum condition for the endoscope. Eq. (2) can be found as follows:

This condition, where the aperture diameter of the variable stop 44 is diminished, is defined in view of the balance between a pan-focus effect by which the depth of field is increased and the reduction of resolving power caused by the diffraction limit of light in the extremely small aperture diameter stated above.

It is assumed that a color filter, such as that shown in FIG. 5, is placed on the surface of the CCD 48. Individual filter elements of this color filter, provided to correspond to individual pixels which give rise to photoelectric conversion, are represented by G for green, Mg for magenta, C for cyan, and Y for yellow. Since the CCD 48 reads out two pixels as one unit in a horizontal direction, a Nyquist rate fn is given by $$fn=1/(2Px) \qquad (3)$$

Generally, in a TV photographing optical system using the CCD, an optical low-pass filter for eliminating moire is placed, and hence there is a need to consider the frequency characteristic of the entire optical system, including this filter.

Where the Nyquist rate is given by Eq. (3), in view of the use of the imaging section 42 having the TV camera function attached to the eyepiece section of the endoscope 41, the filter unit 49 (the optical low-pass filter) disposed in the imaging section 42 is desirable to have frequency characteristics such as those shown in FIG. 6. In this figure, the axis of abscissas is a spatial frequency F (unit: line/mm), while the axis of ordinates is a spatial frequency response represented by MTF (modulation transfer function). A solid curve A represents the spatial frequency characteristic of the optical low-pass filter, while a broken curve B represents the frequency characteristic of an optical system excluding the optical low-pass filter. Although the optical low-pass filter has the characteristic that the response becomes zero at a frequency somewhat lower than the Nyquist rate fn, a spatial frequency fn' at which the MTF is at least 30%, in terms or the Nyquist rate fn of the CCD, is approximated by $$fn' 0.6 fn \qquad (4)$$

This frequency gives an effective resolution limit of the CCD 48.

In contrast to this, the frequency response of the optical system excluding the filter changes with the aperture diameter of the stop, and a diffraction limit (Rayleigh's limit) frequency fr with the optical system is given by $$fr=1/(1.22\lambda F_{NO})=1395\phi/f \qquad (5)$$

where $\lambda=587.56$ nm and $F_{NO}=f/\phi$.

Here, although it is required that the aperture $\phi$ corresponding to the F-number $F_{NO}$ is actually calculated with an effective F-number, the diopter of a rigid endoscope is usually about $-1$ (m$^{-1}$), and therefore an object distance regarding the photographing optical system is in the neighborhood of 1000 mm. Since, in general, the focal length f of the TV photographing optical system for endoscopes is about 10–50 mm, the object distance may be considered to be practically infinite, and the effective F-number can be regarded as about equal to the F-number.

Figure 6:
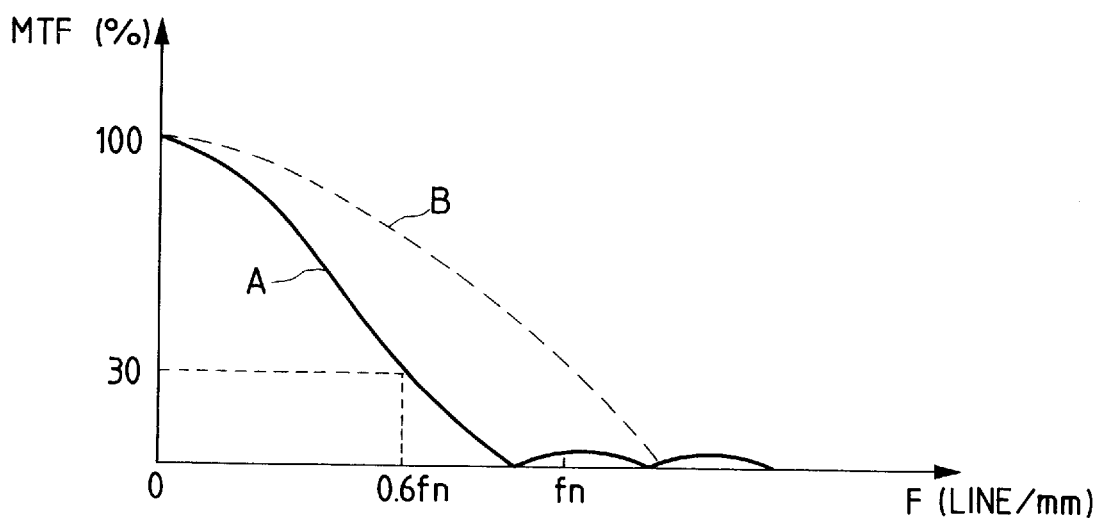
FIG. 6 is a diagram for explaining frequency characteristics of a filter unit placed in an imaging section.

As the aperture diameter of the variable stop 44 is diminished, the diffraction limit frequency becomes low, and the broken curve 13 in FIG. 6 is moved to the left of the figure. Subsequently, when the broken curve B is shifted to the left of the solid curve A, the blurring of an image caused by diffraction becomes prominent. In order to obviate this blurring, it is desirable to satisfy the condition:

$$fn \leq fr \qquad (6)$$

The substitution of Eqs. (3) and (5) in Eq. (6) gives the condition of Eq. (2). If the value of the minimum aperture $\phi$ of the variable stop 44 is below the lower limit of Eq. (2), the degradation of the resolving power will be produced by the influence of diffraction of light as mentioned above, and thus the effect of improvement of the depth of field secured by stopping down the variable stop 44 will not be achieved. However, in the case of a medical endoscope, since the interior of the human body is observed, the degradation of the resolving power by the influence of diffraction of light is not prominent to an observer's expectation. Hence, for Eq. (4), the following condition is satisfactory:

$$fn' 0.42 fn \qquad (4')$$

The reflection of Eq. (4') in Eq. (2) gives $$\phi \geq 1.5 \times 10^{-4} f/Px \qquad (7)$$

Figure 7:
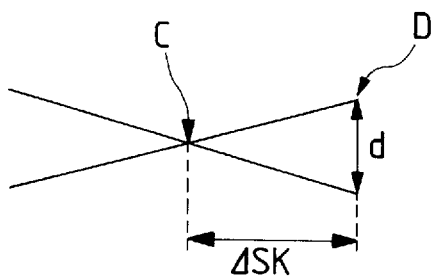
FIG. 7 is a view showing the relationship between an imaging position and the position of an imaging plane relative to an image derived from an endoscope.

Although it has been shown that for the optimum limit of the minimum aperture diameter of the variable stop 44, its lower limit value is defined as the minimum limit value $\phi$ by Eq. (2) or (7), its upper limit value is found as follows:

FIG. 7 shows the relationship between an imaging position C and the position of an imaging plane D relative to an image derived from the endoscope. A focal depth $\Delta SK$ in this case is expressed by $$\Delta SK = d\ F_{NO} = d\ f/\phi \qquad (8)$$

where d is the diameter of a circle of confusion. Eq. (8) can be rewritten as $$\phi = d\ f/\Delta SK \qquad (8')$$

Here, in order to bring the above focus state to a stepping focus every 1 m$^{-1}$, it is favorable that the focal depth $\Delta SK$ satisfies the condition:

$$\Delta SK \geq (1/2)\ f^2/1000 \qquad (9)$$

The relation between the diameter d of the circle of confusion and a spatial frequency Uc for allowing resolution in the optical system is given by $$Uc = 1.22/d \qquad (10)$$

In the present invention, Uc=Um (a Nyquist limit frequency of the CCD 48), and thus when Eq. (3) is used, the diameter d is expressed as $$d = 1.22/Um = 2.44 Px \qquad (11)$$

Hence, from Eqs. (8'), (9), and (11), the following condition is introduced:

$$\phi \leq 4.88 \times 10^{-3} Px/f \qquad (12)$$

Actually, for Eq. (9), the following condition is satisfactory:

$$\Delta SK \geq (1/3) f^2/1000 \qquad (13)$$

As a result, the upper limit value of the minimum aperture diameter of the variable stop 44 becomes $$\phi \leq 7.32 \times 10^{-3} Px/f \qquad (14)$$

Thus, if Eq. (7) is combined with Eq. (14), the optimum range of the minimum limit value φ of the aperture diameter of the variable stop 44 can be found. That is, the range or the minimum limit value φ is given by $$1.5 \times 10^{-4} f/Px \leq \phi \leq 7.32 \times 10^{-3} Px/f \qquad (15)$$

where φ is in millimeters.

Also, it is most appropriate that the focal length f of the optical system is thought of as the total focal length of the optical system placed behind the variable stop 44.

The imaging apparatus of the present invention has been explained on the premise that the stop used is variable, but if brightness is amply sufficient, a fixed aperture stop may be incorporated in the stop unit 45.

According to the present invention, as mentioned above, the imaging apparatus for endoscopes can be realized in which the stop unit 45 placed in the imaging section 42 is equipped with the variable stop 44, and thereby the optimum brightness of the object image is always maintained to optimize the stopping-down effect of the variable stop 44, practically in a pan-focus state that minimizes the burden of a user and without producing the degradation of the resolving power attributable to the diffraction limit.

In the imaging apparatus for endoscopes of the present invention, the surface, closest to the imaging lens system 43, of the glass cover 50 of the imaging section 42 placed at its connection with the endoscope 41 is configured as an aspherical surface for yielding spherical aberration. In this way, aberration yielded when the imaging section 42 is connected with the endoscope 41 is corrected so that the optimum focus position is ensured.

The endoscope 41 relaying the object image to the eyepiece section has a tendency that spherical aberration is undercorrected. Thus, a phenomenon is brought about that as the variable stop 44 of the imaging section 42 is stopped down, a focus position is shifted progressively to a great distance. As such, an aspherical surface which is capable of yielding spherical aberration opposite to that introduced by the endoscope 41, namely, of overcorrecting spherical aberration, is placed close to the variable stop 44 of the imaging section 42. The use of such an aspherical surface brings about the effect that one spherical aberration undercorrected is offset by the other overcorrected, and prevents the focus position from shifting, when the endoscope 41 is connected with the imaging section 42.

Furthermore, in the imaging apparatus for endoscopes of the present invention, if the apparatus is designed so that the actuation of opening and closing of the variable stop 44 is associated with the movement of the focus lens system 46, the optimum observation range will be obtained.

Figure 8:
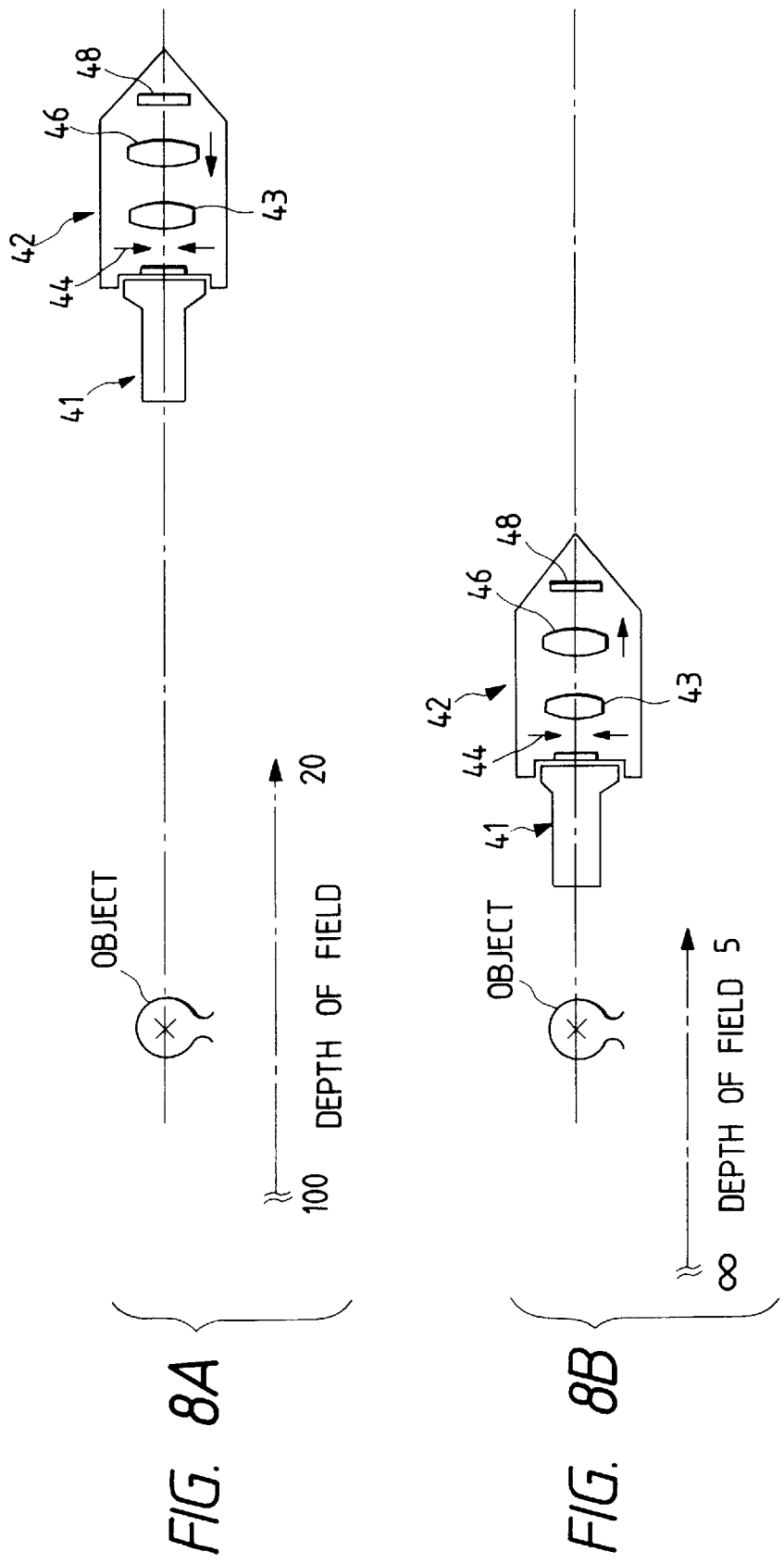
FIGS. 8A and 8B are views for explaining cases where an observation range is optimized by the actuation of a variable stop and the movement of a focus lens system in the imaging apparatus for endoscopes of the present invention.

In general, as illustrated in FIG. 8A, when a distant object is observed, the aperture of the variable stop 44 is opened to obtain a bright observation image, and at the same time, the focus lens system 46 is moved along the optical axis toward the object to bring the distant object to a focus. Conversely, as shown in FIG. 8B, when a nearby object is observed, the variable stop 44 is stopped down with the intention of chiefly increasing the depth of field at a near point, and the focus lens system 46 is moved toward the image so that the focus position is shifted to the near point.

In such cases, a control signal for actuating the variable stop 44 which is transmitted from the CCD 48 is separated, and this separated signal is fed back to the driving portion of the focus lens system 46 to thereby make the movement of the focus lens system 46 synchronized with the actuation of the variable stop 44. The driving portion of the focus lens system 46 may be constructed with a piezo-electric actuator producing strain when a voltage is applied thereto. The control of the driving portion may be exercised through a camera control unit, not shown, or may be done directly or by means of a remote controller through the body of the imaging apparatus for endoscopes. The movement of the focus lens system 46, as well as the actuation of the variable stop 44, may be performed continuously, or discontinuously with respect to optimum observation distances at several points.

Figure 9:
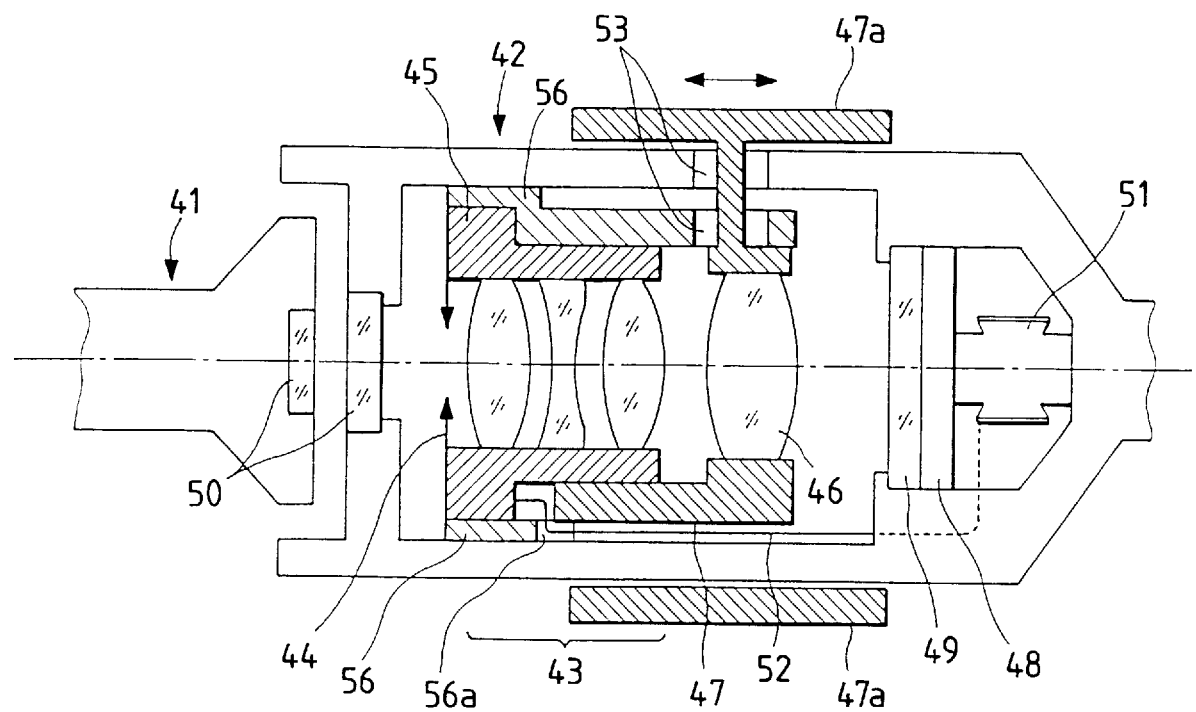
FIG. 9 is a view showing the modification of the imaging apparatus in FIG. 4.

The imaging apparatus for endoscopes shown in FIG. 4 may be constructed as in FIG. 9. In the apparatus shown in FIG. 9, the cylindrical stop unit 45 equipped with the imaging lens system 43 and the variable stop 44 is held, together with the focus lens frame 47 having the focus lens system 46, in a lens barrel 56. The lens barrel 56 and the outer frame of the imaging section 42 are provided with slots 53, through which a member connecting the focus lens frame 47 with the focus ring 47a is passed. In this way, by moving the focus ring 47a in directions of arrows in the figure, the focus lens frame 47 is slid along the optical axis in the lens barrel 56, so that focusing becomes possible. Moreover, the lens barrel 56 is provided with a through-hole 56a, and thus the signal line 52 can be interposed between the outer frame of the imaging section 42 and the focus lens frame 47. The signal line 52 is used to connect the variable stop 44 placed in the stop unit 45 with the flexible printed circuit board 51 placed at the rear end of the CCD 48. Other structural details of this apparatus are the same as in FIG. 4.

Thus, the features of the imaging apparatus shown in FIG. 9 are that the stop unit 45 and the focus lens frame 47 are held by the same lens barrel 56, and the signal line 52 is provided in a space between the outer frame of the imaging section 42 and the focus lens frame 47. Consequently, when the focusing operation is performed, the signal line 52 can be prevented from coming in contact with the moving part of the apparatus, and loads are not applied to the signal line 52 and the flexible printed circuit board 51 connected thereto. Hence, the breaking of the signal line 52 can be obviated.

Figure 10:
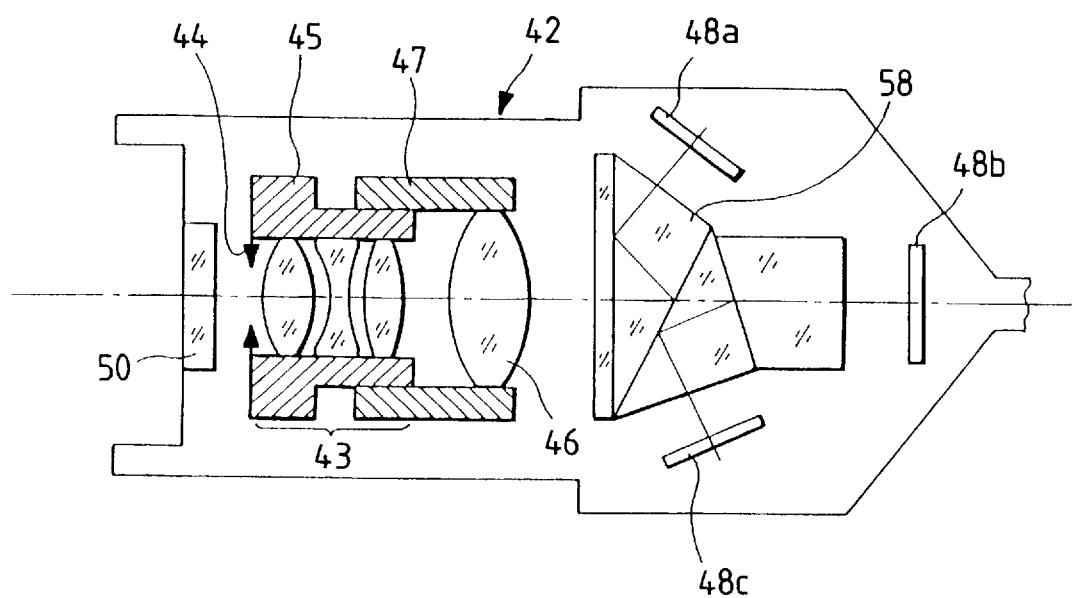
FIG. 10 is a view showing an example where the present invention is applied to an imaging apparatus for endoscopes of a three-imager type.

The apparatus of the present invention can also be designed as an imaging apparatus for endoscopes of a so-called three-imager type. For example, as shown in FIG. 10, the imaging section 42 is equipped with a color separation prism 58 to divide the observation image derived from the endoscope 41 into three color light components of red, blue, and green so that these light components are individually received by a CCD 48a for red, a CCD 48b for blue, and a CCD 48c for green. In such an arrangement, it is desirable that a lens, closest to the object, of the lenses constituting the imaging lens system 43 is configured to hold a positive power and the imaging lens system 43 as a whole, is designed to have a negative power. This is because it is desirable that, in order to hold the ray height of light incident on the imaging lens system 43 as low as possible, the power of this foremost lens of the imaging lens system 43 is positive, and when the imaging lens system 43 is designed to have a negative power in its entirety, the back focal distance can be made relatively long, thus facilitating the placement of the color separation prism 58. In addition, there is the advantage that a space necessary for focusing can be secured.

In accordance with the embodiments shown in the drawings, reference is made to specific arrangements of optical systems and holding members corresponding to some optical systems, provided in the imaging apparatus for endoscopes of the present invention.

First Embodiment

Figure 11:
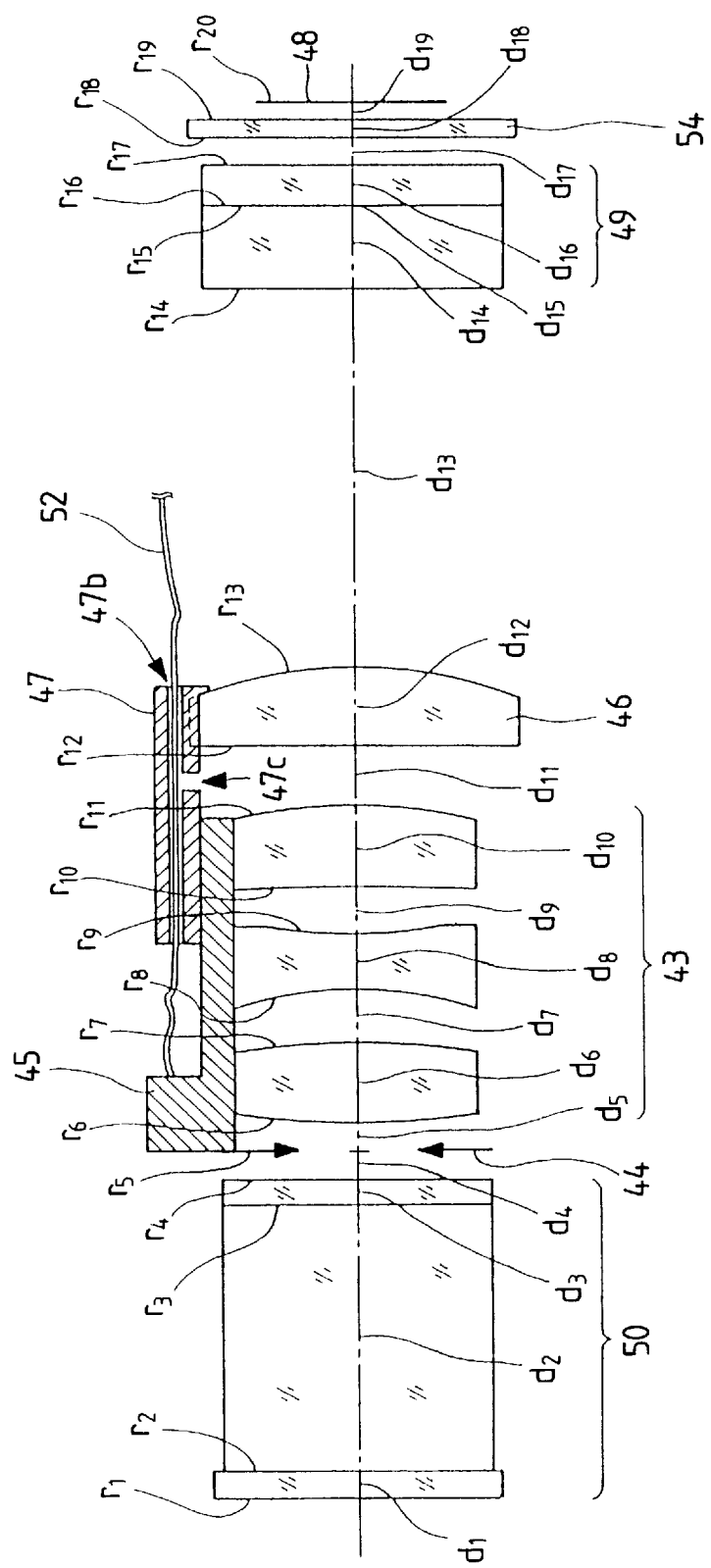
FIG. 11 is a sectional view, developed along the optical axis, showing the arrangement of optical systems and holding members placed in the imaging section of the imaging apparatus for endoscopes of a first embodiment in the present invention.

FIG. 11 shows the arrangement of optical systems and holding members placed in the imaging section of the imaging apparatus for endoscopes of the first embodiment. This imaging section includes, in order from the endoscope side, not shown, the glass cover 50, the variable stop 44, the imaging lens system 43, the focus lens system 46, the filter unit 49, a CCD glass cover 54, and the CCD 48. The variable stop 44 and the imaging lens system 43 are held by the stop unit 45, and their positions are fixed. The CCD 48 is secured in the imaging section. Thus, the relative positions of the variable stop 44, the imaging lens system 43, and the CCD 48 are constant. The focus lens system 46 is retained by the focus lens frame 47, into which the stop unit 45 is fitted. The focusing operation is performed in such a way that the focus ring, not shown, is operated to move the focus lens system 46, together with the focus lens frame 47, along the optical axis. The focus lens frame 47 is provided with the through-hole 47b for passing the signal line 52 connecting the flexible printed circuit board, not shown, placed at the rear end of the CCD 48 and the variable stop 44. The focus lens frame 47 is also provided with the air hole 47c communicating with the through-hole 47 to adjust air pressure in the focus lens frame 47 when the focusing operation is performed.

In the imaging lens system 43, a lens placed closest to the object (on the leftmost side in the figure), namely the foremost lens, has a positive power and the entire system possesses a negative power. The focus lens system 46 is composed of a single positive lens.

The following is the numerical data of optical members shown in FIG. 11

---

The focal length $f_o$ of the imaging lens system 43 = −335.023
The focal length $f_a$ of the focus lens system 46 = 18.027
The total focal length f of the optical system placed behind the variable stop 44 = 18.899
The pixel pitch Px in the horizontal scanning direction of the CCD 48 = 4.75 μm
$|f_a/f_o|$ = 0.054

| | | | |
|---|---|---|---|
| $r_1 = \infty$ | $d_1 = 1.0500$ | $n_1 = 1.51633$ | $v_1 = 64.15$ |
| $r_2 = \infty$ | $d_2 = 9.8000$ | $n_2 = 1.77250$ | $v_2 = 49.60$ |
| $r_3 = \infty$ | $d_3 = 1.0000$ | $n_3 = 1.56384$ | $v_3 = 60.70$ |
| $r_4 = 989.0000$ | $d_4 = 1.0000$ | | |
| $r_5 = \infty$ | $d_5 = 1.0000$ | | |
| (the variable stop 44) | | | |
| $r_6 = 25.3600$ | $d_6 = 3.0000$ | $n_6 = 1.72916$ | $v_6 = 54.68$ |
| $r_7 = -25.9200$ | $d_7 = 2.0000$ | | |
| $r_8 = -10.8433$ | $d_8 = 2.0000$ | $n_8 = 1.75520$ | $v_8 = 27.51$ |
| $r_9 = 15.7979$ | $d_9 = 1.7000$ | | |
| $r_{10} = -133.5447$ | $d_{10} = 3.0000$ | $n_{10} = 1.76200$ | $v_{10} = 40.10$ |
| $r_{11} = -16.7274$ | $d_{11} = 2.0394$ | | |
| $r_{12} = 131.7501$ | $d_{12} = 2.9674$ | $n_{12} = 1.72916$ | $v_{12} = 54.68$ |
| $r_{13} = -14.4628$ | $d_{13} = 14.0000$ | | |
| $r_{14} = \infty$ | $d_{14} = 3.0800$ | $n_{14} = 1.54814$ | $v_{14} = 45.78$ |
| $r_{15} = \infty$ | $d_{15} = 0.0500$ | | |
| $r_{16} = \infty$ | $d_{16} = 1.6000$ | $n_{16} = 1.51400$ | $v_{16} = 74.00$ |
| $r_{17} = \infty$ | $d_{17} = 1.0000$ | | |
| $r_{18} = \infty$ | $d_{18} = 0.7500$ | $n_{18} = 1.51633$ | $v_{18} = 64.15$ |
| $r_{19} = \infty$ | $d_{19} = 0.9600$ | | |
| $r_{20} = \infty$ | | | |

---

Second Embodiment

Figure 12:
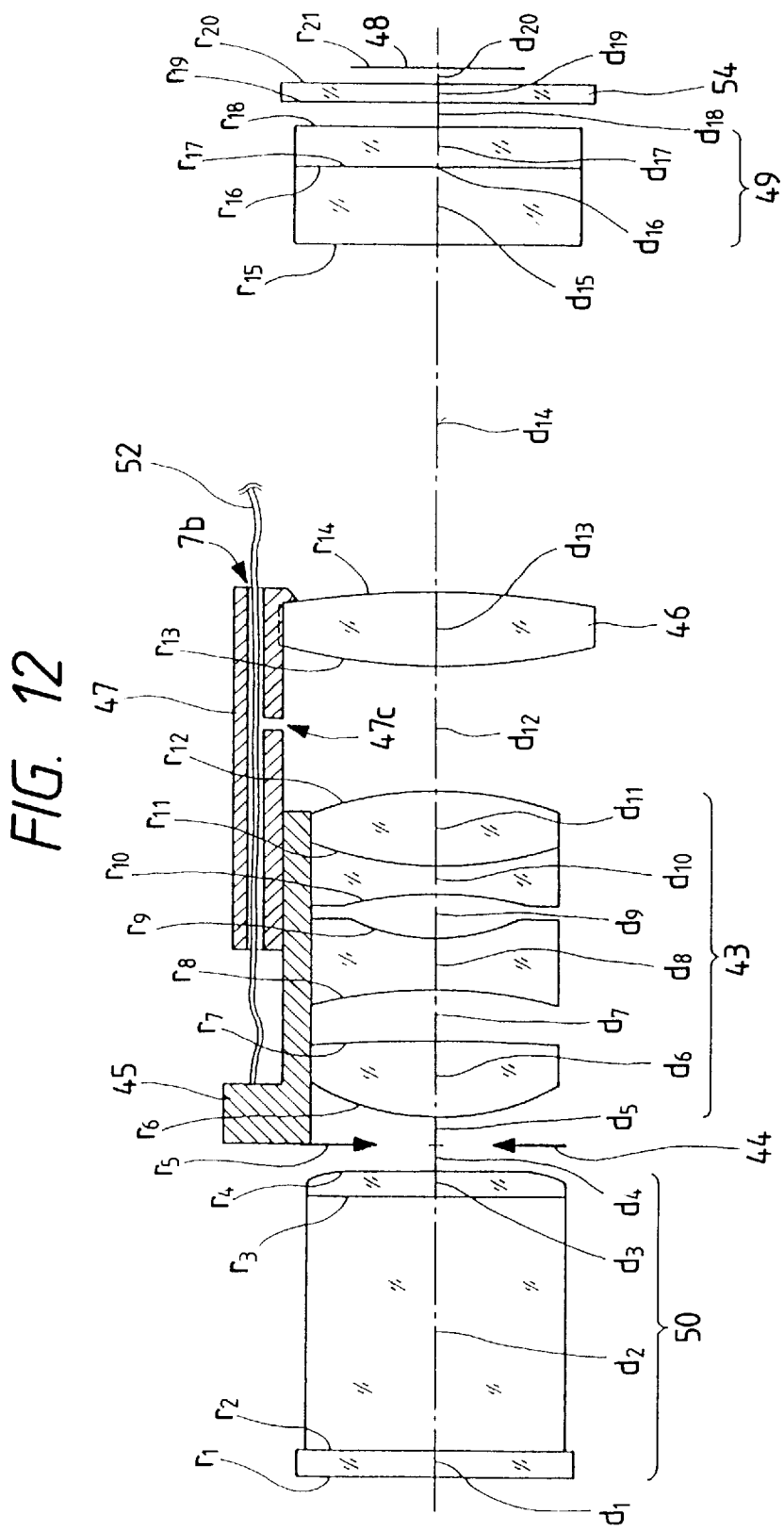
FIG. 12 is a sectional view, developed along the optical axis, showing the arrangement of optical systems and holding members placed in the imaging section of the imaging apparatus for endoscopes of a second embodiment in the present invention.

FIG. 12 shows the arrangement of optical systems and holding members placed in the imaging section of the imaging apparatus for endoscopes of the second embodiment. In this embodiment, a surface, closest to the imaging lens system 43, of the glass cover 50, namely the rearmost surface thereof, is configured as an aspherical surface, while a lens, closest to the CCD 48, of the imaging lens system 43, namely the rearmost lens thereof, is constructed with a cemented lens. With the exception of these points, the second embodiment has the same arrangement as the first embodiment.

The following is the numerical data of optical members shown in FIG. 12.

---

The focal length $f_o$ of the imaging lens system 43 = −150.056
The focal length $f_a$ of the focus lens system 46 = 16.192
The total focal length f of the optical system placed behind the variable stop 44 = 23.921
The pixel pitch Px in the horizontal scanning direction of the CCD 48 = 4.75 μm
$|f_a/f_o|$ = 0.108

| | | | |
|---|---|---|---|
| $r_1 = \infty$ | $d_1 = 1.0$ | $n_1 = 1.7725$ | $v_1 = 49.6$ |
| $r_2 = \infty$ | $d_2 = 9.8000$ | $n_2 = 1.77250$ | $v_2 = 49.60$ |
| $r_3 = \infty$ | $d_3 = 1.0000$ | $n_3 = 1.56384$ | $v_3 = 60.70$ |
| $r_4 = 989.0000$ | $d_4 = 1.0000$ | | |
| (aspherical) | | | |
| $r_5 = \infty$ | $d_5 = 1.0000$ | | |
| (the variable stop 44) | | | |
| $r_6 = 7.8549$ | $d_6 = 2.9977$ | $n_6 = 1.68893$ | $v_6 = 31.08$ |
| $r_7 = -138.7952$ | $d_7 = 2.0000$ | | |
| $r_8 = -14.0470$ | $d_8 = 1.8975$ | $n_8 = 1.76200$ | $v_8 = 40.10$ |
| $r_9 = 6.7063$ | $d_9 = 1.7000$ | | |
| $r_{10} = -11.5108$ | $d_{10} = 1.0000$ | $n_{10} = 1.78472$ | $v_{10} = 25.71$ |
| $r_{11} = 11.1255$ | $d_{11} = 2.9519$ | $n_{11} = 1.72916$ | $v_{11} = 54.68$ |
| $r_{12} = -10.7126$ | $d_{12} = 4.6085$ | | |
| $r_{13} = 19.8622$ | $d_{13} = 2.9431$ | $n_{13} = 1.72916$ | $v_{13} = 54.68$ |
| $r_{14} = -27.2932$ | $d_{14} = 13.1300$ | | |
| $r_{15} = \infty$ | $d_{15} = 3.0800$ | $n_{15} = 1.54814$ | $v_{15} = 45.78$ |
| $r_{16} = \infty$ | $d_{16} = 0.0500$ | | |
| $r_{17} = \infty$ | $d_{17} = 1.6000$ | $n_{17} = 1.51400$ | $v_{17} = 74.00$ |
| $r_{18} = \infty$ | $d_{18} = 1.0000$ | | |
| $r_{19} = \infty$ | $d_{19} = 0.7500$ | $n_{19} = 1.51633$ | $v_{19} = 64.15$ |
| $r_{20} = \infty$ | $d_{20} = 0.9600$ | | |
| $r_{21} = \infty$ | | | |

Aspherical coefficients
Fourth surface
$A_4 = 4.3568 \times 10^{-4}$, $A_6 = -7.4319 \times 10^{-5}$

---

Third Embodiment

Figure 13:
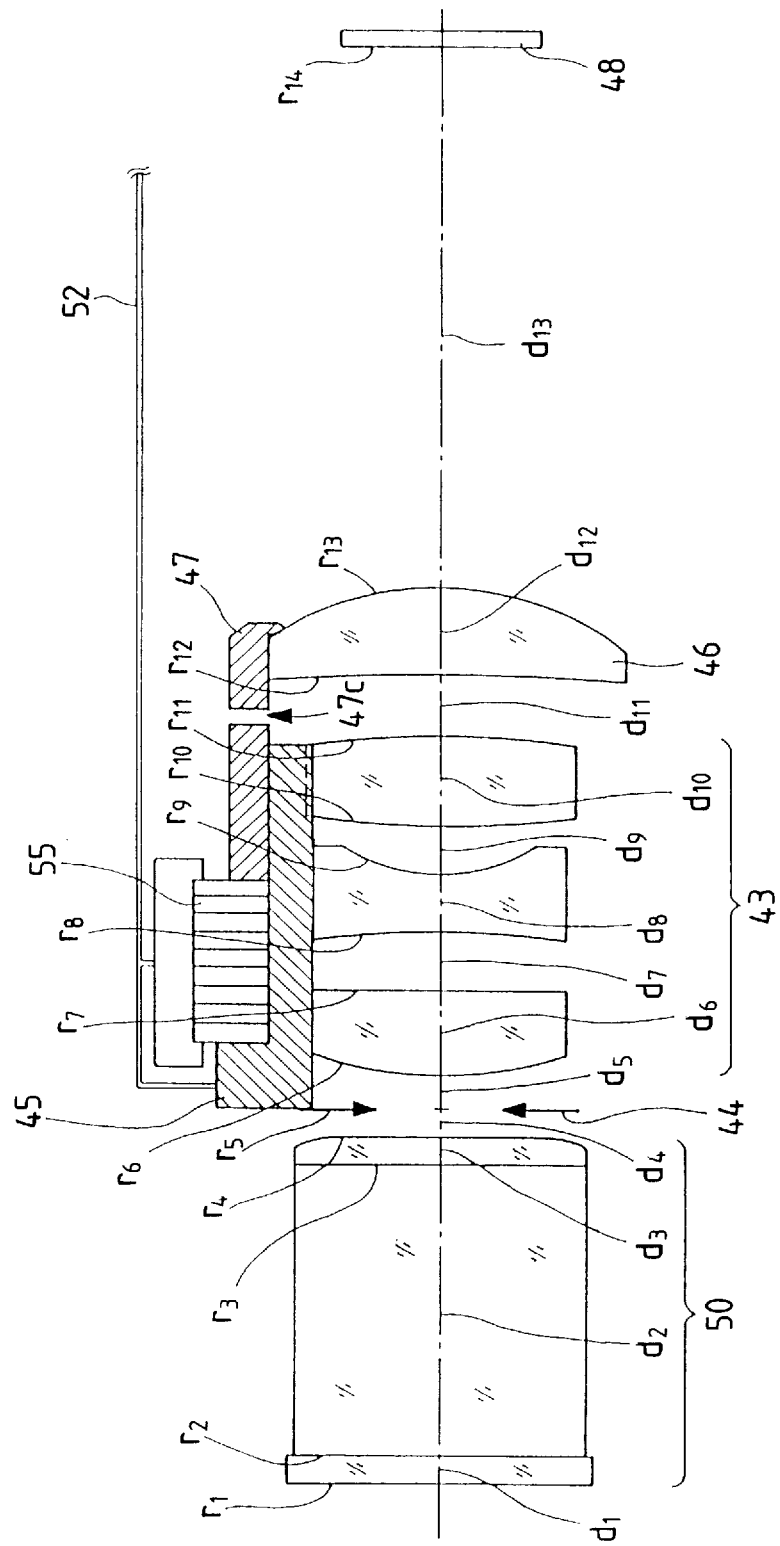
FIG. 13 is a sectional view, developed along the optical axis, showing the arrangement of optical systems and holding members placed in the imaging section of the imaging apparatus for endoscopes of a third embodiment in the present invention.

FIG. 13 shows the arrangement; of optical systems and holding members placed in the imaging section of the imaging apparatus for endoscopes of the third embodiment. This imaging section includes, in order from the endoscope side, not shown, the glass cover 50, the variable stop 44, the imaging lens system 43, the focus lens system 46, and the CCD 48. The variable stop 44 and the imaging lens system 43 are held by the stop unit 45, and their positions are fixed. The CCD 48 is secured in the imaging section. Thus, the relative positions of the variable stop 44, the imaging lens system 43, and the CCD 48 are constant. The focus lens system 46 is retained by the focus lens frame 47, into which the stop unit 45 is fitted. The focus lens frame 47 is provided with the air hole 47c for adjusting air pressure in the focus lens frame 47 when the focusing operation is performed.

In the apparatus of the third embodiment, a signal produced in the CCD 48 is used to control the aperture diameter of the variable stop 44 and thereby the focusing operation is performed. Thus, the control of the aperture diameter of the variable stop 44 can be associated with the focusing operation. The endoscope, in which an object illuminated by an illumination device is observed, has the feature that when the distal end of the endoscope is moved close to the object, the field is brightened, while when it is moved farther away, the field is darkened. In this way, information on the brightness of the image obtained from the CCD 48 can be utilized for focusing control. Specifically, in the apparatus of the third embodiment, the stop unit 45 is fitted into the focus lens frame 47 through a piezoelectric actuator 55 producing strain when a voltage is applied thereto. The piezoelectric actuator 55 is connected to the signal line 52 through a voltage converting circuit, not shown, for converting an electric signal into the voltage. Thus, the object image from the endoscope is once formed on the CCD 48, arid the electric signal converted on the information of light of this image is further converted into the voltage. By doing so, a focusing state of the object image is determined. If the focusing state is not normal, the piezoelectric actuator 55 is driven to move the focus lens system 46, together with the focus lens frame 47, along the optical axis, thereby making a focusing adjustment.

In the imaging lens system 43, a lens placed closest to the object (on the leftmost side i t the figure), namely the foremost lens, has a positive power and the entire system possesses a negative power. The focus lens system 46 is composed of a single positive lens. The glass cover 50 is made of crystal glass with heat resistance, such as sapphire, quartz, rock crystal, etc. Also, the surface, closest to the imaging lens system 43, of the glass cover 50, namely the rearmost surface thereof, is configured as an aspherical surface having the function of correcting for spherical aberration introduced by the endoscope.

The following is the numerical data of optical members shown in FIG. 13.

---

The focal length $f_o$ of the imaging lens system 43 = -38.308
The focal length $f_a$ of the focus lens system 46 = 12.496
The total focal length f of the optical system placed behind the variable stop 44 = 18.900
The pixel pitch Px in the horizontal scanning direction of the CCD 48 = 4.75 μm
$|f_a/f_o|$ = 0.33

| | | | |
|---|---|---|---|
| $r_1 = \infty$ | $d_1 = 1.0$ | $n_1 = 1.7725$ | $v_1 = 49.6$ |
| $r_2 = \infty$ | $d_2 = 9.8000$ | $n_2 = 1.77250$ | $v_2 = 49.60$ |
| $r_3 = \infty$ | $d_3 = 1.0000$ | $n_3 = 1.56384$ | $v_3 = 60.70$ |
| $r_4 = 989.0000$ | $d_4 = 1.0000$ | | |
| (aspherical) | | | |
| $r_5 = \infty$ | $d_5 = 1.0000$ | | |
| (the variable stop 44) | | | |
| $r_6 = 11.1474$ | $d_6 = 3.0000$ | $n_6 = 1.72916$ | $v_6 = 54.68$ |
| $r_7 = \infty$ | $d_7 = 2.0000$ | | |
| $r_8 = -28.1387$ | $d_8 = 2.0000$ | $n_8 = 1.75520$ | $v_8 = 27.51$ |
| $r_9 = 5.0528$ | $d_9 = 1.7000$ | | |
| $r_{10} = 42.0446$ | $d_{10} = 3.0000$ | $n_{10} = 1.76200$ | $v_{10} = 40.10$ |
| $r_{11} = -34.6990$ | $d_{11} = 2.0653$ | | |
| $r_{12} = -86.4013$ | $d_{12} = 3.0118$ | $n_{12} = 1.72916$ | $v_{12} = 54.68$ |
| $r_{13} = -8.3636$ | $d_{13} = 19.526$ | | |
| $r_{14} = \infty$ | | | |

Aspherical coefficients
Fourth surface
$A_4 = 4.3568 \times 10^{-4}, A_6 = -7.4319 \times 10^{-5}$

---

Fourth Embodiment

Figure 14:
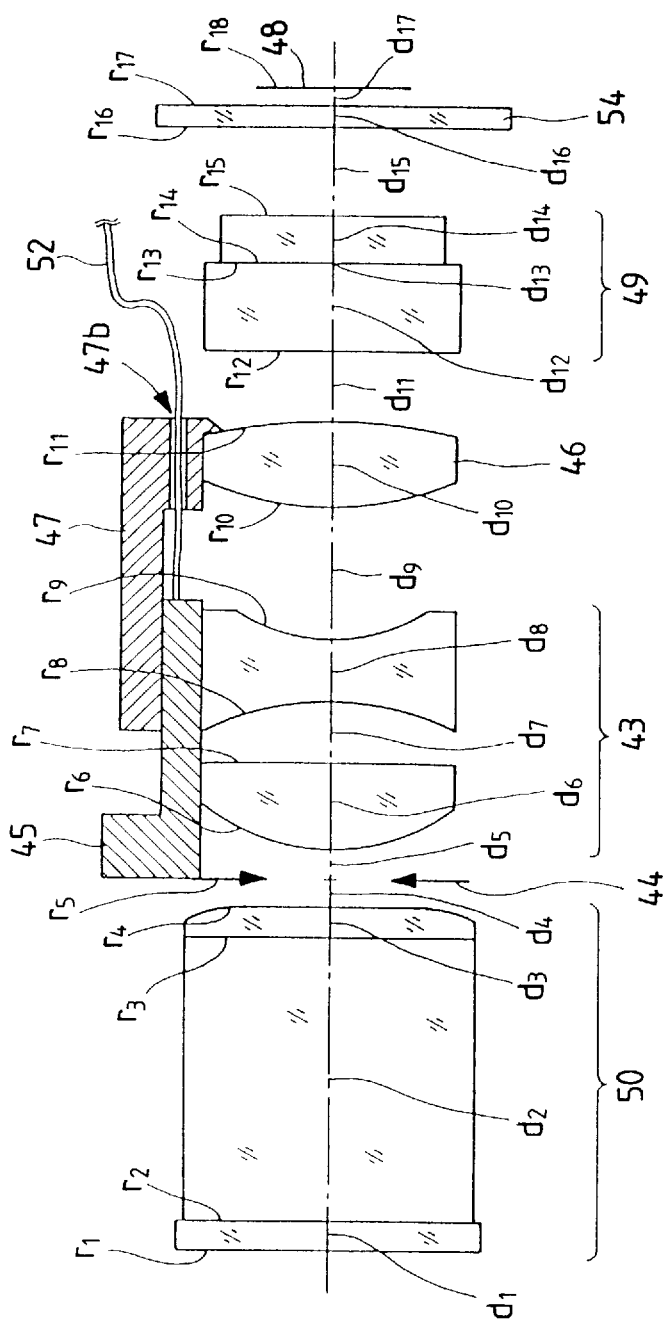
FIG. 14 is a sectional view, developed along the optical axis, showing the arrangement of optical systems and holding members placed in the imaging section of the imaging apparatus for endoscopes of a fourth embodiment in the present invention.

FIG. 14 shows the arrangement of optical systems and holding members placed in the imaging section of the imaging apparatus for endoscopes of the fourth embodiment. In this embodiment, aberration is allowable to such an extent that there is no problem in practical use, and thereby the number of lenses is decreased and the structures of the mechanical frames are simplified to intend cost reduction. The imaging lens system 43 is composed of two lenses, and the through-hole 47b bored through the focus lens frame 47 which holds the focus lens system 46 and into which the stop unit 45 is fitted, also serves as the air hole for adjusting air pressure in the focus lens frame 47 when the focusing operation is performed. In this way, the frame structures are simplified. The surface, closest to the imaging lens system 43, of the glass cover 50, namely the rearmost surface thereof, is aspherical. With the exception of these points, the fourth embodiment has almost the same arrangement as the first embodiment.

The fourth embodiment, as mentioned above, is designed to reduce the number of lenses constituting the imaging lens system 43 and to simplify the structures of the holding members of respective lens systems, and thus is advantageous to costs.

The following is the numerical data of optical members shown in FIG. 14.

---

The focal length $f_o$ of the imaging lens system 43 = -101.096
The focal length $f_a$ of the focus lens system 46 = 8.698
The total focal length f of the optical system placed behind the variable stop 44 = 18.996
The pixel pitch Px in the horizontal scanning direction of the CCD 48 = 4.75 μm
$|f_a/f_o|$ = 0.086

| | | | |
|---|---|---|---|
| $r_1 = \infty$ | $d_1 = 1.0500$ | $n_1 = 1.51633$ | $v_1 = 64.15$ |
| $r_2 = \infty$ | $d_2 = 9.8000$ | $n_2 = 1.77250$ | $v_2 = 49.60$ |
| $r_3 = \infty$ | $d_3 = 1.0000$ | $n_3 = 1.56384$ | $v_3 = 60.70$ |
| $r_4 = 989.0000$ | $d_4 = 0.9500$ | | |
| (aspherical) | | | |
| $r_5 = \infty$ | $d_5 = 1.0000$ | | |
| (the variable stop 44) | | | |
| $r_6 = 6.3668$ | $d_6 = 3.0000$ | $n_6 = 1.72916$ | $v_6 = 54.68$ |
| $r_7 = -180.7528$ | $d_7 = 2.0000$ | | |
| $r_8 = -7.8316$ | $d_8 = 2.0000$ | $n_8 = 1.75520$ | $v_8 = 27.51$ |
| $r_9 = 5.1019$ | $d_9 = 4.5000$ | | |
| $r_{10} = 9.9451$ | $d_{10} = 3.0000$ | $n_{10} = 1.76200$ | $v_{10} = 40.10$ |
| $r_{11} = -17.2809$ | $d_{11} = 2.3300$ | | |
| $r_{12} = \infty$ | $d_{12} = 3.0800$ | $n_{12} = 1.54814$ | $v_{12} = 45.78$ |
| $r_{13} = \infty$ | $d_{13} = 0.0500$ | | |
| $r_{14} = \infty$ | $d_{14} = 1.6000$ | $n_{14} = 1.51400$ | $v_{14} = 74.00$ |
| $r_{15} = \infty$ | $d_{15} = 3.0000$ | | |
| $r_{16} = \infty$ | $d_{16} = 0.7500$ | $n_{16} = 1.51633$ | $v_{16} = 64.15$ |
| $r_{17} = \infty$ | $d_{17} = 0.9600$ | | |
| $r_{18} = \infty$ | | | |

Aspherical coefficients
Fourth surface
$A_4 = 4.3568 \times 10^{-4}, A_6 = -7.4319 \times 10^{-5}$

---

Fifth Embodiment

Figure 15:
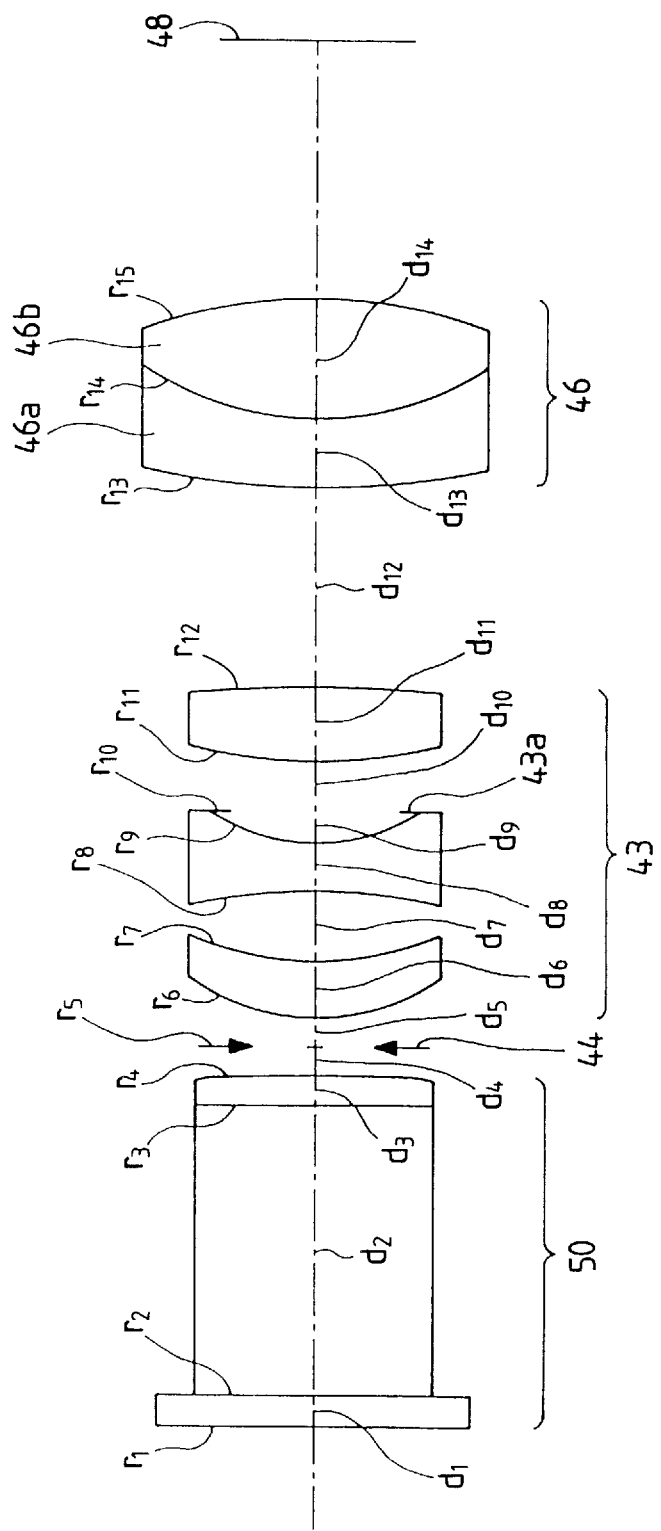
FIG. 15 is a sectional view, developed along the optical axis, showing the arrangement of optical systems placed in the imaging section of the imaging apparatus for endoscopes of a fifth embodiment in the present invention.

FIG. 15 shows the arrangement of optical systems placed in the imaging section of the imaging apparatus for endoscopes of the fifth embodiment. This embodiment is an example of an optical system used when the color separation prism 58, such as that shown in FIG. 10, is placed in the imaging section of the apparatus. Although the members for holding the corresponding optical systems are not shown in FIG. 15, any of the holding members in the above embodiments is applicable to the fifth embodiment.

The imaging section of the apparatus of the fifth embodiment includes, in order from the endoscope side, not shown, the glass cover 50, the variable stop 44, the imaging lens system 43, the focus lens system 46, and the CCD 48. A flare stop 43a is disposed on the exit side of a middle lens of the lens unit constituting the imaging lens system 43.

Here, the color separation prism, although it is not specified in FIG. 15, is interposed between the focus lens system 46 and the CCD 48. Thus, it is desirable that the lens, closest to the object, of lenses constituting the imaging lens system 43, namely the foremost lens thereof, is configured as a positive lens and the imaging lens system 43 is designed to have a negative power as a whole. This is because it is desirable that in order to hold the ray height of light incident on the imaging lens system 43 as low as possible, the power of this foremost lens of the imaging lens system 43 is positive, and by designing the imaging lens system 43 so that its entire system has a negative power, the back focal distance can be made relatively long, thus facilitating the placement of the color separation prism. In addition, there is the advantage that a space necessary for focusing can be secured.

Further, the surface, closest to the variable stop 44, of the glass cover 50, namely the rearmost surface thereof, is configured as an aspherical surface to correct for aberration. Still further, the focus lens system 46 is constructed with an achromatic, positive cemented lens including a negative lens 46a and a positive lens 46b.

The following is the numerical data of optical members shown in FIG. 15.

```
The focal length f₀ of the imaging lens system 43 = -147.902
The outside diameter of the imaging lens system 43 = 8
The focal length fₐ of the focus lens system 46 = 23.915
The outside diameter of the focus lens system 46 = 11
The total focal length f of the optical system placed behind the
variable stop 44 = 24.916
The pixel pitch Px in the horizontal scanning direction of the CCD
48 = 6.35 μm
|fₐ/f₀| = 0.162
r₁ = ∞            d₁ = 1.0500      n₁ = 1.51633    v₁ = 64.14
r₂ = ∞            d₂ = 9.8000      n₂ = 1.77250    v₂ = 49.60
r₃ = ∞            d₃ = 1.0000      n₃ = 1.56384    v₃ = 60.70
r₄ = 989.0000     d₄ = 0.9500
(aspherical)
r₅ = ∞            d₅ = 1.0000
(the variable stop 44)
r₆ = 6.3130       d₆ = 2.0000      n₆ = 1.80610    v₆ = 40.92
r₇ = 9.6080       d₇ = 2.4000
r₈ = -15.4010     d₈ = 1.6000      n₈ = 1.64769    v₈ = 33.79
r₉ = 5.9220       d₉ = 1.1400
r₁₀ = ∞           d₁₀ = 1.6600
r₁₁ = 15.4010     d₁₁ = 2.6000     n₁₁ = 1.71999   v₁₁ = 50.22
r₁₂ = -33.1580    d₁₂ = 6.8400
r₁₃ = 25.4410     d₁₃ = 2.3000     n₁₃ = 1.64769   v₁₃ = 33.79
r₁₄ = 9.2310      d₁₄ = 4.1000     n₁₄ = 1.51633   v₁₄ = 64.14
r₁₅ = -16.0100
Aspherical coefficients
Fourth surface
A₄ = 4.3568 × 10⁻⁴, A₆ = -7.4319 × 10⁻⁵
```

In the numerical data of the embodiments mentioned above, $r_1$, $r_2$, represent radii of curvature of individual lens or member surfaces; $d_1$, $d_2$, . . . represent thicknesses of individual lenses or members, or spaces therebetween; $n_1$, $n_2$, . . . represent refractive indices of individual lenses or members; $v_1$, $v_2$, . . . represent Abbe's numbers of individual lenses or members; and $A_4$ and $A_6$ represent aspherical coefficients.

Also, the configuration of the aspherical surface in each embodiment is given by $$Z = \frac{Y^2/r}{1 + \sqrt{1 - (Y/r)^2}} + A_4 Y^4 + A_6 Y^6$$

where Z is the coordinate in the direction of the optical axis, Y is the coordinate in the direction normal to the optical axis, and r is the radius of curvature.

What is claimed is:

1. An imaging apparatus for endoscope comprising:
   an endoscope relaying an object image through an observing optical system; and
   an imaging section removably mounted to a rearmost end of said endoscope, including a stop unit provided with a variable stop whose aperture size is variable, an imaging lens system, a focus lens system, and an image sensor,
   relative positions of said variable stop, said imaging lens system, and said image sensor being constant, and
   said focus lens system being movable along an optical axis of said imaging section.

2. An imaging apparatus for endoscopes according to claim 1, wherein said imaging lens system is held in said stop unit.

3. An imaging apparatus for endoscopes according to claim 2, wherein said focus lens system is held in a focus lens frame, and said stop unit is fitted into said focus lens frame.

4. An imaging apparatus for endoscopes according to claim 3, wherein said focus lens frame is provided with a through-hole for a signal line transmitting a signal for controlling the aperture size of said variable stop.

5. An imaging apparatus for endoscopes according to claim 4, wherein a minimum outside diameter of said focus lens system is equal to an outside diameter of said imaging lens system.

6. An imaging apparatus for endoscopes according to claim 5, wherein said focus lens system includes a single lens.

7. An imaging apparatus for endoscopes according to claim 6, wherein said imaging lens system includes at least one cemented lens.

8. An imaging apparatus for endoscopes according to claim 7, wherein a foremost lens of said imaging lens system has a positive power and said imaging lens system has a negative power as a whole.

9. An imaging apparatus for endoscopes according to claim 8, wherein the following condition is satisfied:

$$0.05 < |f_a/f_o| < 0.35$$

where $f_o$ is a focal length of said imaging lens system and $f_a$ is a focal length of said focus lens system.

10. An imaging apparatus for endoscopes according to claim 9, wherein a minimum aperture diameter φ of said variable stop satisfies the following condition:

$$1.5 \times 10^{-4} f/Px \leq \phi \leq 7.32 \times 10^{-3} Px/f$$

where f is a total focal length of an optical system placed behind said variable stop and Px is a pixel pitch in a horizontal direction of said image sensor.

11. An imaging apparatus for endoscopes according to claim 10, wherein an optical member for correcting for spherical aberration is disposed close to said variable stop.

12. An imaging apparatus for endoscopes according to claim 11, wherein an actuation of opening and closing of said variable stop is associated with a movement of said focus lens system along an optical axis.

13. An imaging apparatus for endoscopes according to claim 12, wherein each of said endoscope and said imaging section is hermetically sealed through a member having resistance to water vapor of high temperature and pressure.

14. An imaging apparatus for endoscopes according to claim 13, wherein said imaging section further includes a color separation prism and image sensors corresponding to color light components divided by said color separation prism.

15. An imaging apparatus for endoscopes according to claim 2, wherein said imaging lens system and said focus lens system are held in an imaging lens frame and a focus lens frame, respectively, said imaging lens frame and said focus lens frame being held in a single lens barrel.

* * * * *